United States Patent [19]
Owens

[11] Patent Number: 5,962,485
[45] Date of Patent: Oct. 5, 1999

[54] N-(2-BENZYLOXY-1-PHENETHYL)-N-(2'-METHOXYETHYL)AMINO-METHANE COMPOUNDS ARE USEFUL AS TACHYKININ ANTAGONISTS

[75] Inventor: Andrew Pate Owens, Rushden, United Kingdom

[73] Assignee: Merck Sharp & Dohme Ltd., Hoddesdon, United Kingdom

[21] Appl. No.: 08/913,567

[22] PCT Filed: Mar. 13, 1996

[86] PCT No.: PCT/GB96/00586

§ 371 Date: Sep. 16, 1997

§ 102(e) Date: Sep. 16, 1997

[87] PCT Pub. No.: WO96/29317

PCT Pub. Date: Sep. 26, 1996

[30] Foreign Application Priority Data

Mar. 18, 1995 [GB] United Kingdom .................... 9505492

[51] Int. Cl.⁶ .......................... A61K 31/41; C07D 249/04
[52] U.S. Cl. ............................................. 514/359; 548/255
[58] Field of Search ............................... 548/255; 514/359

[56] References Cited

FOREIGN PATENT DOCUMENTS 0 577 394    1/1994    European Pat. Off. .
WO 93/24465  12/1993   WIPO .

*Primary Examiner*—Laura L. Stockton
*Attorney, Agent, or Firm*—J. Eric Thies; David L. Rose

[57] ABSTRACT

The subject N-(2-benzyloxy-1-phenethyl)-N-(2'-methoxyethyl)amino-methane compounds of the formula:

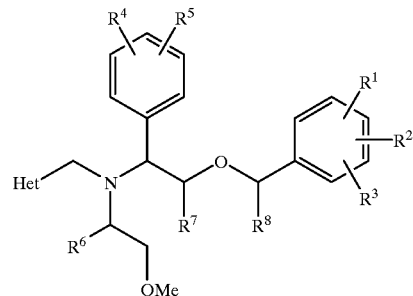

(wherein $R^1$, $R^2$, $R^3$, $R^4$, $R^5$, $R^6$, $R^7$, $R^8$ and Het are defined herein) are tachykinin receptor antagonists which are useful in the treatment of pain, inflammation, migraine and emesis.

19 Claims, No Drawings

N-(2-BENZYLOXY-1-PHENETHYL)-N-(2'-METHOXYETHYL)AMINO-METHANE COMPOUNDS ARE USEFUL AS TACHYKININ ANTAGONISTS

This application is a 371 of PCT/GB96/00586 filed Mar. 13, 1996.

This invention relates to a class of heteroaromatic compounds which are useful as tachykinin antagonists.

The tachykinins are a group of naturally occurring peptides found widely distributed throughout mammalian tissues, both within the central nervous system and in peripheral nervous and circulatory systems.

At present, there are three known mammalian tachykinins referred to as substance P, neurokinin A (NKA, substance K, neuromedin L) and neurokinin B (NKB, neuromedin K) (for review see J. E. Maggio, *Peptides* (1985) 6(suppl. 3), 237–242). The current nomenclature designates the three tachykinin receptors mediating the biological actions of substance P, NKA and NKB as the $NK_1$, $NK_2$ and $NK_3$ receptors, respectively.

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, *J. Auton. Pharmacol.* (1993) 13, 23–93.

For instance, substance P is believed inter alia to be involved in the neurotransmission of pain sensations [Otsuka et al, "Role of Substance P as a Sensory Transmitter in Spinal Cord and Sympathetic Ganglia" in 1982 *Substance P in the Nervous System*, Ciba Foundation Symposium 91, 13–34 (published by Pitman) and Otsuka and Yanagisawa, "Does Substance P Act as a Pain Transmitter?" *TIPS* (1987) 8, 506–510], specifically in the transmission of pain in migraine (B. E. B. Sandberg et al, *J. Med Chem*, (1982) 25, 1009) and in arthritis [Levine et al *Science* (1984) 226, 547–549]. Tachykinins have also been implicated in gastrointestinal (GI) disorders and diseases of the GI tract such as inflammatory bowel disease [Mantyh et al *Neuroscience* (1988) 25(3), 817–37 and D. Regoli in "*Trends in Cluster Headache*" Ed. Sicuteri et al Elsevier Scientific Publishers, Amsterdam (1987) page 85)] and emesis [F. D. Tattersall et al, *Eur. J. Pharmacol.*, (1993) 250, R5-R6]. It is also hypothesised that there is a neurogenic mechanism for arthritis in which substance P may play a role [Kidd et al "A Neurogenic Mechanism for Symmetrical Arthritis" in *The Lancet*, Nov. 11, 1989 and Grönblad et al, "Neuropeptides in Synovium of Patients with Rheumatoid Arthritis and Osteoarthritis" in *J. Rheumatol.* (1988) 15(12), 1807–10]. Therefore, substance P is believed to be involved in the inflammatory response in diseases such as rheumatoid arthritis and osteoarthritis, and fibrositis [O'Byrne et al, *Arthritis and Rheumatism* (1990) 33, 1023–8]. Other disease areas where tachykinin antagonists are believed to be useful are allergic conditions [Hamelet et al, *Can. J. Pharmacol. Physiol.* (1988) 66, 1361–7], immunoregulation [Lotz et al, *Science* (1988) 241, 1218–21 and Kimball et al, *J. Immunol.* (1988) 141(10), 3564–9] vasodilation, bronchospasm, reflex or neuronal control of the viscera [Mantyh et al, *PNAS* (1988) 85, 3235–9] and, possibly by arresting or slowing β-amyloid-mediated neurodegenerative changes [Yankner et al, *Science* (1990) 250, 279–82] in senile dementia of the Alzheimer type, Alzheimer's disease and Down's Syndrome.

Tachykinin antagonists may also be useful in the treatment of small cell carcinomas, in particular small cell lung cancer (SCLC) [Langdon et al, *Cancer Research* (1992) 52, 4554–7].

Substance P may also play a role in demyelinating diseases such as multiple sclerosis and amyotrophic lateral sclerosis [J. Luber-Narod et al, poster C.I.N.P. XVIIIth Congress, Jun. 28th–Jul. 2nd, 1992], and in disorders of bladder function such as bladder detrusor hyper-reflexia (*Lancet*, May 16th 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosus (European patent specification no. 0 436 334), ophthalmic disease such as conjuctivitis, vernal conjunctivitis, and the like, and cutaneous diseases such as contact dermatitis, atopic dermatitis, urticaria, and other eczematoid dermatitis (European patent specification no. 0 394 989).

European patent specification no. 0 577 394 (published Jan. 5th, 1994) discloses morpholine and thiomorpholine tachykinin receptor antagonists of the general formula

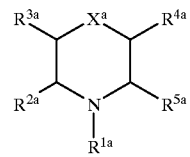

wherein $R^{1a}$ is a large variety of substituents;

$R^{2a}$ and $R^{3a}$ are inter alia hydrogen;

$R^{4a}$ is inter alia

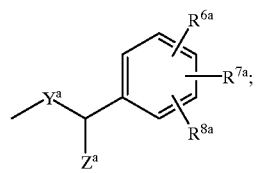

$R^{5a}$ is inter alia optionally substituted phenyl;

$R^{6a}$, $R^{7a}$ and $R^{8a}$ are a variety of substituents;

$X^a$ is O, S, SO or $SO_2$;

$Y^a$ is inter alia O; and $Z^a$ is hydrogen or $C_{1-4}$alkyl.

We have now found a further class of non-peptides which are potent antagonists of tachykinins, especially of substance P.

The present invention provides compounds of the formula (I):

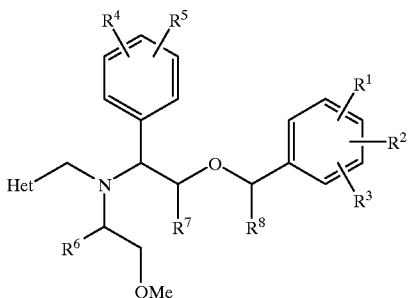

wherein

R$^1$ represents hydrogen, halogen, C$_{1-6}$alkyl, C$_{2-6}$alkenyl, C$_{2-6}$alkynyl, C$_{3-7}$cycloalkyl, C$_{3-7}$cycloalkylC$_{1-4}$alkyl, C$_{1-6}$alkoxy, C$_{1-4}$alkyl substituted by a hydroxy or C$_{1-4}$alkoxy group, OCF$_3$, hydroxy, trifluoromethyl, trimethylsilyl, nitro, CN, SR$^a$, SOR$^a$, SO$_2$R$^a$, COR$^a$, CO$_2$R$^a$ or CONR$^a$R$^b$ where R$^a$ and R$^b$ are each independently hydrogen or C$_{1-4}$alkyl;

R$^2$ and R$^3$ each independently represent hydrogen, halogen, C$_{1-6}$alkyl, C$_{1-6}$alkoxy substituted by a C$_{1-4}$alkoxy group, or trifluoromethyl;

R$^4$ represents hydrogen, halogen, C$^{2-6}$alkyl, C$^{1-6}$alkenyl, C$_{2-6}$alkynyl, C$_{3-7}$cycloalkyl, C$_{3-7}$cycloalkylC$_{1-4}$alkyl, C$_{1-6}$alkoxy, C$_{1-4}$alkyl substituted by a hydroxy or C$_{1-4}$alkoxy group, OCF$_3$, hydroxy, trifluoromethyl, trimethylsilyl, nitro, CN, SR$^a$, SOR$^a$, SO$_2$R$^a$, COR$^a$, CO$_2$R$^a$, CONR$^a$R$^b$ where R$^a$ and R$^b$ are as previously defined;

R$^5$ represents hydrogen, halogen, C$_{1-6}$alkyl, C$_{1-6}$alkoxy substituted by a C$_{1-4}$alkoxy group, or trifluoromethyl;

R$^6$, R$^7$ and R$^8$ each independently represent hydrogen or a C$_{1-4}$alkyl group optionally substituted by a hydroxy group;

Het represents a 5- or 6-membered heterocyclic ring containing 2 or 3 nitrogen atoms optionally substituted by =O, =S or a C$_{1-4}$alkyl group, and optionally substituted by a group of the formula ZNR$^9$R$^{10}$ where Z is C$_{1-6}$alkylene or C$_{3-6}$cycloalkyl;

R$^9$ is hydrogen or C$_{1-4}$alkyl, C$_{3-7}$cycloalkyl, C$_{3-7}$cycloalkylC$_{1-4}$alkyl, or C$_{2-4}$alkyl substituted by C$_{1-4}$alkoxy or hydroxyl;

R$^{10}$ is hydrogen or C$_{1-4}$alkyl, C$_{3-7}$cycloalkyl, C$_{3-7}$cycloalkylC$_{1-4}$alkyl, or C$_{2-4}$alkyl substituted by C$_{1-4}$alkoxy, hydroxyl or a 4, 5 or 6 membered heteroaliphatic ring containing one or two heteroatoms selected from N, O and S;

or R$^9$, R$^{10}$ and the nitrogen atom to which they are attached form a heteroaliphatic ring of 4 to 7 ring atoms, optionally substituted by one or two groups selected from hydroxy or C$_{1-4}$alkoxy optionally substituted by a C$_{1-4}$alkoxy or hydroxyl group, and optionally containing a double bond, which ring may optionally contain an oxygen or sulphur ring atom, a group S(O) or S(O)$_2$ or a second nitrogen atom which will be part of a NH or NR$^c$ moiety where R$^c$ is C$_{1-4}$alkyl optionally substituted by hydroxy or C$_{1-4}$alkoxy;

or R$^9$, R$^{10}$ and the nitrogen atom to which they are attached form a non-aromatic azabicyclic ring system of 6 to 12 ring atoms;

or Z, R$^9$ and the nitrogen atom to which they are attached form a heteroaliphatic ring to 4 to 7 ring atoms which may optionally contain an oxygen ring atom;

and pharmaceutically acceptable salts thereof.

Certain particularly apt compounds of the present invention include those wherein R$^1$ is hydrogen, C$_{1-4}$alkyl, C$_{1-4}$alkoxy, halogen or CF$_3$.

Most aptly R$^2$ is hydrogen, C$_{1-4}$alkyl, C$_{1-4}$alkoxy, halogen or CF$_3$.

Most aptly R$^3$ is hydrogen, fluorine, chlorine or CF$_3$.

Favourably R$^1$ is fluorine, chlorine or CF$_3$.

Favourably R$^2$ is hydrogen, fluorine, chlorine or CF$_3$.

Favourably R$^3$ is hydrogen, fluorine, chlorine or CF$_3$.

Preferably R$^1$ and R$^2$ are in the 3 and 5 positions of the phenyl ring.

More preferably, R$^1$ is 3-fluoro or 3-CF$_3$.

More preferably, R$^2$ is 5-fluoro or 5-CF$_3$.

More preferably, R$^3$ is hydrogen.

Most preferably, R$^1$ is 3-F or 3-CF$_3$, R$^2$ is 5-F or 5-CF$_3$ and R$^3$ is hydrogen.

Most aptly R$^4$ is hydrogen.

Most aptly R$^5$ is hydrogen, fluorine, chlorine or CF$_3$.

Preferably R$^4$ is hydrogen and R$^5$ is hydrogen or 4-fluoro.

Most aptly R$^6$ and R$^7$ are each independently hydrogen or methyl.

Preferably R$^6$ is hydrogen. Preferably R$^7$ is hydrogen. Most preferably R$^6$ and R$^7$ are both hydrogen.

Most aptly R$^8$ may be hydrogen or C$_{1-2}$alkyl optionally substituted by a hydroxy group. In particular, R$^8$ may be hydrogen, methyl or hydroxymethyl.

Favourably Het is a 5-membered ring.

In particular, Het may represent a heterocyclic ring selected from:

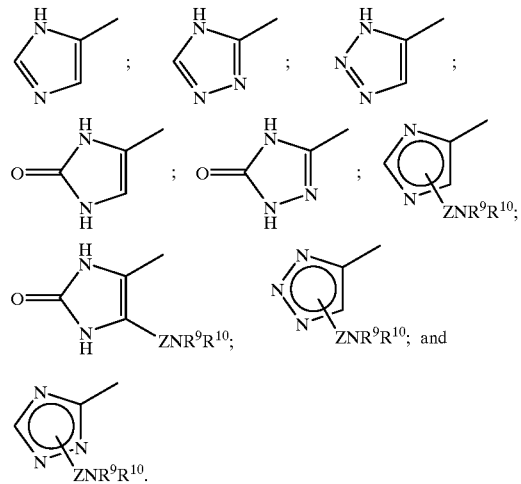

Particularly preferred heterocyclic rings represented by R$^6$ are selected from:

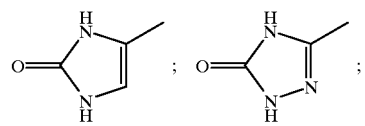

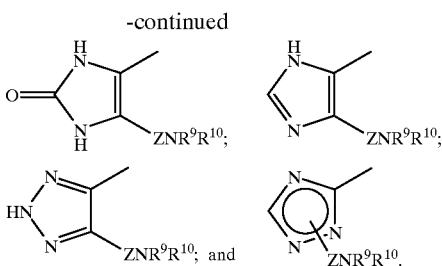

Most especially, Het may represent a heterocyclic ring selected from:

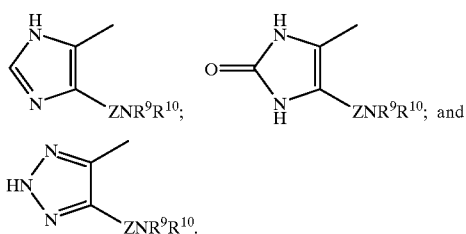

A particularly preferred heterocyclic ring represented by Het is:

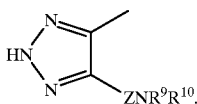

With respect to compounds of the formula (I), Z may be a linear, branched or cyclic group. Favourably Z contains 1 to 4 carbon atoms and most favourably 1 or 2 carbon atoms. A particularly favourable group Z is $CH_2$.

With respect to compounds of the formula (I), $R^9$ may aptly be a $C_{1-4}$alkyl group or a $C_{2-4}$alkyl group substituted by a hydroxyl or $C_{1-2}$alkoxy group, $R^{10}$ may aptly be a $C_{1-4}$alkyl group or a $C_{1-4}$alkyl group substituted by a hydroxyl or $C_{1-2}$alkoxy group, or $R^9$ and $R^{10}$ may be linked so that, together with the nitrogen atom to which they are attached, they form an azetidinyl, pyrrolidinyl, piperidyl, morpholino, thiomorpholino, piperazino or piperazino group substituted on the nitrogen atom by a $C_{1-4}$alkyl group or a $C_{2-4}$alkyl group substituted by a hydroxy or $C_{1-2}$alkoxy group.

Where the group $NR^9R^{10}$ represents a heteroaliphatic ring of 4 to 7 ring atoms and said ring contains a double bond, a particularly preferred group is 3-pyrroline.

Where the group $NR^9R^{10}$ represents a non-aromatic azabicyclic ring system, such a system may contain between 6 and 12, and preferably between 7 and 10, ring atoms. Suitable rings include 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.2.2]decyl, 7-azabicyclo[4.3.1]decyl, 7-azabicyclo[4.4.1]undecyl and 8-azabicyclo[5.4.1]dodecyl, especially 5-azabicyclo[2.2.1]heptyl and 6-azabicyclo[3.2.1]octyl.

Where $R^{10}$ represents a $C_{2-4}$alkyl group substituted by a 5 or 6 membered heteroaliphatic ring containing one or two heteroatoms selected from N, O and S, suitable rings include pyrrolidino, piperidino, piperazino, morpholino, or thiomorpholino. Particularly preferred are nitrogen containing heteroaliphatic rings, especially pyrrolidino and morpholino rings.

Particularly suitable moieties $ZNR^9R^{10}$ include those wherein Z is $CH_2$ or $CH_2CH_2$ and $NR^9R^{10}$ is amino, methylamino, dimethylamino, diethylamino, azetidinyl, pyrrolidino and morpholino.

Further preferred moieties represented by $ZNR^9R^{10}$ are those wherein Z is $CH_2$ or $CH_2CH_2$, $R^9$ represents hydrogen, $C_{1-4}$alkyl or $C_{3-6}$cycloalkyl and $R^{10}$ is $C_{2-4}$alkyl substituted by one or two substituents selected from hydroxy, $C_{1-2}$alkoxy, azetidinyl, pyrrolidino, piperidino, morpholino or thiomorpholino.

In particular, Z is preferably $CH_2$ and $NR^9R^{10}$ is preferably dimethylamino, azetidinyl or pyrrolidino, especially dimethylamino.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The cycloalkyl groups referred to herein may represent, for example, cyclopropyl, cyclobutyl, cyclopentyl or cyclohexyl. A suitable cycloalkylalkyl group may be, for example, cyclopropylmethyl.

As used herein, the terms "alkenyl" and "alkynyl" as a group or part of a group means that the group is straight or branched. Examples of suitable alkenyl groups include vinyl and allyl. A suitable alkynyl group is propargyl.

When used herein the term halogen means fluorine, chlorine, bromine and iodine. The most apt halogens are fluorine and chlorine of which fluorine is preferred.

One favoured group of compounds of the present invention are of the formula (Ia):

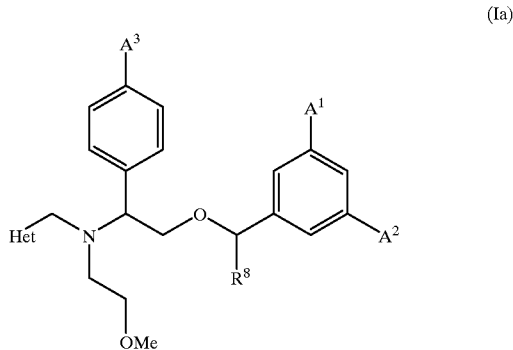

(Ia)

wherein
$R^8$ and Het are as defined in relation to formula (I) and
$A^1$ is fluorine or $CF_3$;
$A^2$ is fluorine or $CF_3$; and
$A^3$ is hydrogen or fluorine;
and pharmaceutically acceptable salts thereof.

Specific compounds within the scope of this invention include:

4-(N-((2-((3,5-bis(trifluoromethyl)phenyl)methyloxy)-1-(S)-phenyl)ethyl-N-(2'-methoxyethyl))aminomethyl)-5-(N',N'-dimethylaminomethyl)-1,2,3-triazole;

and pharmaceutically acceptable salts thereof.

In a further aspect of the present invention, the compounds of formula (I) will preferably be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of the formula (I) will have the preferred stereochemistry as shown in formula (Ib)

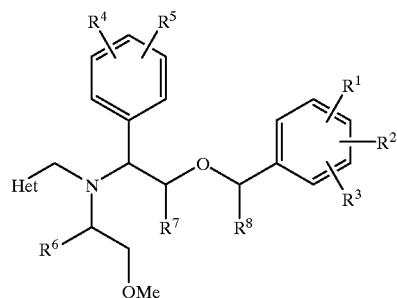

(Ib)

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example gylcerol or glucose, to adjust the tonicity of the emulsion. Suitable emulsions will typically contain up to 20% oil, for example, between 5 and 20%. The fat emulsion will preferably comprise fat droplets between 0.1 and 1.0 $\mu$m, particularly 0.1 and 0.5 $\mu$m, and have a pH in the range of 5.5 to 8.0.

Particularly preferred emulsion compositions are those prepared by mixing a compound of formula (I) with Intrahpid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastrooesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances*, Eds. J. Kucharczyk et al, CRC Press Inc., Boca Raton, Florida, USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide. Additionally, a compound of formula (I) may be administered in combination with an anti-inflammatory corticosteroid, such as dexamethasone. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. pharmacol.*, (1993) 250, R5-R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and headache, including migraine, acute or chronic tension headache, cluster headache, temporomandibular pain, and maxillary sinus pain.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor antagonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene $D_4$ antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-$HT_1$ agonists, especially sumatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an anti-inflammatory agent such as a bradykinin receptor antagonist.

The present invention also provides a composition comprising a compound of formula (I), a bronchodilator, and a pharmaceutically acceptable carrier.

It will be appreciated that for the treatment or prevention of pain or nociception, a compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof. Preferred salts of these opioid analgesics include morphine sulphate, morphine hydrochloride, morphine tartrate, codeine phosphate, codeine sulphate, dihydrocodeine bitartrate, diacetylmorphine hydrochloride, hydrocodone bitartrate, hydromorphone hydrochloride, levorphanol tartrate, oxymorphone hydrochloride, alfentanil hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 1 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to a general process (A), the compounds according to the invention may be prepared from compounds of formula (II)

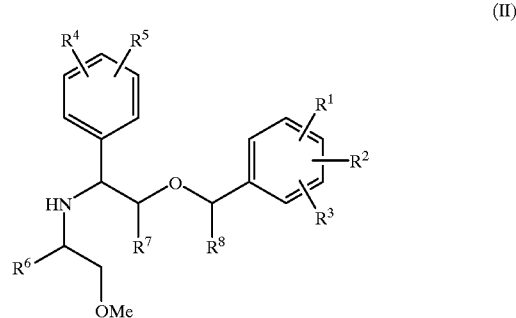

(II)

wherein $R^1$, $R^2$, $R^3$, $R^4$, $R^5$, $R^6$, $R^7$ and $R^8$ are as defined in relation to formula (I) by reaction with a compound of formula (III):

LG-$CH_2$-Het'  (III)

where Het' is a group of the formula Het as defined in relation to formula (I) or a precursor therefor and LG is a leaving group such as an alkyl- or arylsulphonyloxy group (e.g. mesylate or tosylate) or a halogen atom (e.g. bromine, chlorine or iodine); and, if Het' is a precursor group, converting it to a group Het (in which process any reactive group may be protected and thereafter deprotected if desired).

This reaction may be performed in conventional manner, for example in an organic solvent such as dimethylformamide in the presence of an acid acceptor such as potassium carbonate.

Thus, for instance, compounds in which Het is a 2-oxo-1,3-imidazolyl, 1,3-imidazolyl or 1,2,3-triazolyl group, each of which is substituted by ZNR$^9$R$^{10}$, may be prepared by the reaction of a compound of formula (II) with a compound of formula (IV)

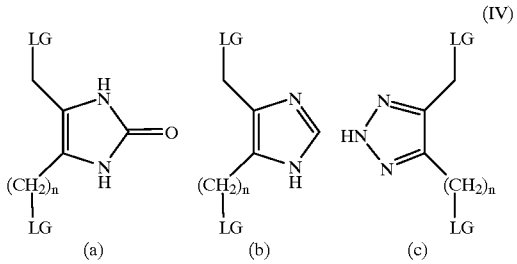

(IV)

where n is an integer from 1 to 6, and each LG independently represents a leaving group as previously defined, followed by reaction of the resultant compound with an amine of formula NHR$^9$R$^{10}$ to complete the group ZNR$^9$R$^{10}$.

It will be appreciated that, where necessary, reactive groups may be protected, thus for example, the NH groups of an imidazolone of formula (IVa) may be protected by any suitable amine protecting group such as an acetyl group.

According to another process (B), compounds of formula (I) wherein Het represents 1,2,3-triazol-4-yl substituted by CH$_2$NR$^9$R$^{10}$, may be prepared by reaction of a compound of formula (V)

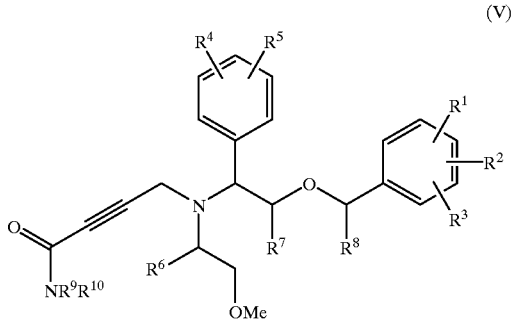

(V)

with an azide, for example, sodium azide in a suitable solvent such as dimethylsulphoxide at a temperature of between 40° C. and 100° C., followed by reduction of the carbonyl group adjacent to —NR$^9$R$^{10}$ using a suitable reducing agent such as lithium aluminium hydride at at a temperature between −10° C. and room temperature, conveniently at room temperature.

Alternatively, according to a process (C), compounds of formula (I) wherein Het represents 1,2,3-triazol-4-yl substituted by CH$_2$NR$^9$R$^{10}$, may be prepared by reaction of a compound of formula (VI)

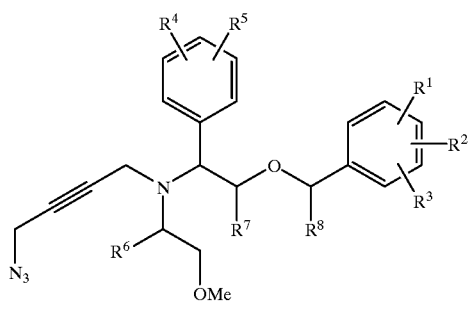

(VI)

with an amine of formula NHR$^9$R$^{10}$, in a suitable solvent such as an ether, for example, dioxan, at elevated temperature, for example, between 50° C. and 100° C., in a sealed tube, or the like. This reaction is based upon that described in *Chemische Berichte* (1989) 122, p. 1963.

According to another process, (D), compounds of formula (I) wherein Het represents substituted or unsubstituted 1,3,5-triazine may be prepared by reaction of intermediates of formula (VII):

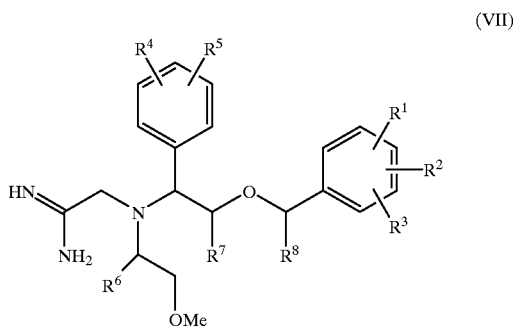

(VII)

with substituted or unsubstituted 1,3,5-triazine.

The reaction is conveniently effected in a suitable organic solvent, such as acetonitrile, at elevated temperature, such as 80–90° C., preferably about 82° C.

According to a further process, (E), compounds of formula (I) wherein Het represents substituted or unsubstituted 1,2,4-triazine may be prepared by reaction of an intermediate of formula (VIII) with a dicarbonyl compound of formula (IX):

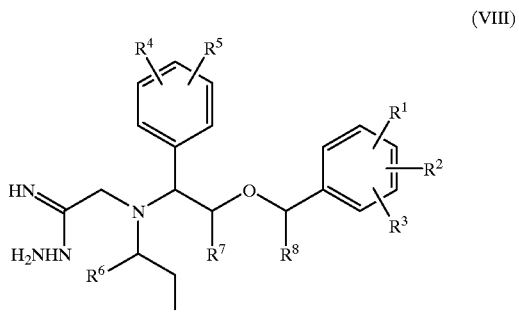

(VIII)

-continued

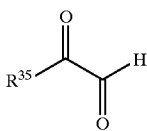
(IX)

wherein $R^{35}$ represents H or a suitable substituent such as $ZNR^9R^{10}$.

The reaction is conveniently effected in a suitable organic solvent, such as an ether, e.g. tetrahydrofuran, conveniently at ambient temperature.

According to a further process (F), compounds of formula (I) wherein Het represents a substituted 1,2,4-triazolyl group may be prepared by reaction of an intermediate of formula (II) with a compound of formula (X)

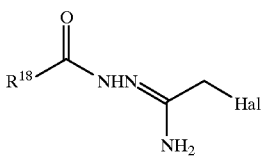
(X)

wherein Hal is a halogen atom, for example, bromine, chlorine or iodine and $R^{18}$ is H, $CONH_2$ or $OCH_3$ (which is converted to an oxo substituent under the reaction conditions), in the presence of a base, followed where necessary by conversion to a compound of formula (I), for example, by reduction of the $CONH_2$ group to $CH_2NH_2$.

Suitable bases of use in the reaction include alkali metal carbonates such as, for example, potassium carbonate. The reaction is conveniently effected in an anhydrous organic solvent such as, for example, anhydrous dimethylformamide, preferably at elevated temperature, such as about 140° C.

A suitable reducing agent for the group $CONH_2$ is lithium aluminium hydride, used at between −10° C. and room temperature.

According to another process, (G), compounds of formula (I) wherein Het represents thioxotiiazolyl may be prepared from intermediates of formula (XI)

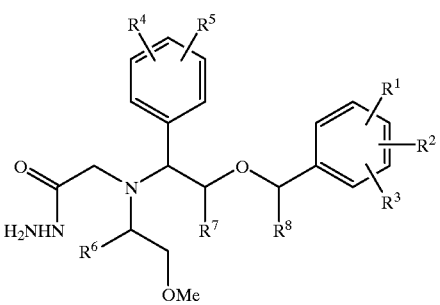
(XI)

by reaction with a compound of formula HNCS, in the presence of a base.

Suitable bases of use in the reaction include organic bases such as, for example, 1,8-diazabicyclo[5.4.0]undec-7-ene (DBU). The reaction is conveniently effected in a suitable organic solvent, such as alcohol, e.g. butanol.

Further details of suitable procedures will be found in the accompanying Examples.

Intermediates of formula (V) may be prepared from intermediates of formula (II) by reaction with an acetylene compound of formula $HC\equiv C\text{-}CH_2\text{-}Hal$ in the presence of a base such as potassium carbonate in a suitable solvent such as dimethylformamide, conveniently at room temperature, followed by reaction of the resultant acetylene intermediate with an amide of formula $Hal\text{-}CO\text{-}NR^9R^{10}$ in the presence of suitable catalysts including bis(triphenylphosphine)palladium(II) chloride, copper(I) iodide and triphenylphosphine in a suitable solvent such as triethylamine, preferably at reflux.

Intermediates of formula (VI) may be prepared from a compound of formula (XII)

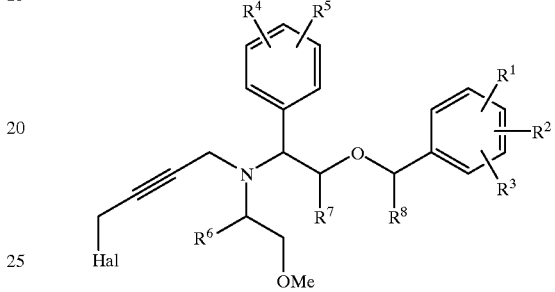
(XII)

wherein Hal is a halogen atom, for example, chlorine, bromine or iodine, especially chlorine, by reaction with an azide, for example, sodium azide in a suitable solvent such as dimethylsulphoxide at or below room temperature.

Compounds of formula (XII) may be prepared by a dropwise addition of an intermediate of formula (II) to a dihaloacetylene of formula $Hal\text{-}CH_2\text{-}C\equiv C\text{-}CH_2\text{-}Hal$ where each Hal is independently chlorine, bromine or iodine, especially chlorine. The reaction is conveniently effected in a suitable solvent such as dimethylformamide in the presence of a base such as potassium carbonate.

Intermediates of formula (VII) may be prepared from intermediates of formula (II) by reaction with a compound of formula $Hal\text{-}CH_2\text{-}C(NH)NH_2$, where Hal is as previously defined.

Intermediates of formula (VIII) may be prepared from intermediates of formula (II) by reaction with a compound of formula $Hal\text{-}CH_2\text{-}C(NH)NHNH\text{-}Boc$, wherein Hal is as previously defined and Boc stands for t-butoxycarbonyl, followed by deprotection under acidic conditions.

Compounds of formula (IX) are commercially available or may be prepared from commercially available compounds by known methods.

Compounds of formula (X) may be prepared as described in J. Med. Chem., (1984) 27, 849.

Intermediates of formula (XI) may be prepared from the corresponding ester by treatment with hydrazine. The reaction is conveniently effected in a suitable organic solvent, such as an alcohol, for example, ethanol, at elevated temperature.

For compounds wherein Het is a heterocycle substituted by a $ZNR^9R^{10}$ group where Z is $CH_2$, certain favoured compounds of formula (I) may be prepared from a corresponding compound with a hydrogen atom in place of the $ZNR^9R^{10}$. Thus, for example a compound of the formula (I) wherein Het is an imidazolinone group carrying a $CH_2NR^9R^{10}$ moiety may be prepared from a corresponding compound lacking the $CH_2NR^9R^{10}$ moiety by reaction with formaldehyde and an amine $NHR^9R^{10}$ under conventional Mannich reaction conditions, for example in methanol with heating. If desired a pre-formed reagent such as $R^9R^{10}N^+=CH_2.I^-$ may be employed and a tertiary amine such as triethylamine used as acid acceptor.

Alternatively a compound of formula (I) wherein Het is an imidazolinone group lacking a $CH_2NR^9R^{10}$ may be reacted with paraformaldehyde and an amine for example a secondary amine such as pyrrolidine to give a compound wherein the imidazolinone ring is substituted by $CH_2NR^9R^{10}$ where $R^9$, $R^{10}$ and the nitrogen atom to which they are attached form a heteroaliphatic ring of 4 to 7 ring atoms which may optionally contain an oxygen ring atom or a second nitrogen atom which will be part of a NH or $NR^c$ moiety, where $R^c$ is as previously defined.

This reaction may be performed in a conventional manner, for instance, in a suitable solvent such as an alcohol, for example, methanol at an elevated temperature up to the boiling point of the solvent.

Intermediates of formula (II) may be prepared by reaction of a compound of formula (XIII) with a compound of formula (XIV):

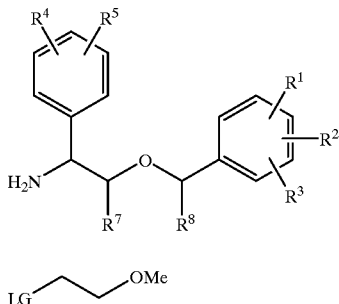

(XIII)

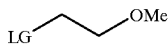

(XIV)

wherein $R^1$, $R^2$, $R^3$, $R^4$, $R^5$, $R^7$ and $R^8$ are as defined in relation to formula (I) and LG is as previously defined. Preferably LG is a halogen atom, expecially a bromine atom.

The reaction is effected in a conventional manner, for example in an organic solvent such as dimethylformamide in the presence of a base such as, for example, an alkali metal hydride, such as sodium hydride.

Compounds of formula (XIII) may be prepared from known starting materials by the reaction of a compound of formula (XV) with a compound of formula (XVI), followed by removal of the N-protecting group:

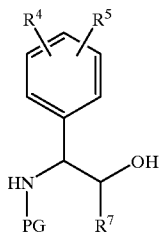

(XV)

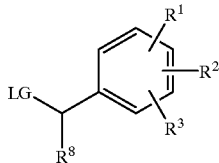

(XVI)

where LG is as previously defined and PG is a conventional amine protecting group, such as tert-butoxycarbonyl. The reaction is conveniently effected in a suitable organic solvent, such as dimethylformide in the presence of a base, such as, for example, an alkali metal hydride, such as sodium hydride. Removal of the protecting group will depend upon the choice of protecting group. A tert-butoxycarbonyl group may be removed, for instance, using trifluoroacetic acid.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the $NK_1$ receptor of less than 1 $\mu$M on said test method.

The following non-limiting Examples serve to illustrate the preparation of compounds of the present invention:

EXAMPLE 1

4-(N-((2-((3,5-Bis(trifluoromethyl)phenyl)methyloxy)-1-(S)-phenyl)ethyl-N-(2'-methoxyethyl))aminomethyl)-5-(N',N'-dimethylaminomethyl)-1,2,3-triazole a) (2S)-1-((3,5-Bis(trifluoromethyl)phenyl)methyloxy)-2-(2'-methoxyethylamino)-2-phenylethane L-2-Ammonium-1-(3',5'-bis(trifluoromethyl)phenyl)methyloxy-2-phenylethane (2 g) was dissolved in dimethylformamide (10 ml). Sodium hydride (264 mg, 60%) was added followed by 2-bromoethyl methyl ether (1.2 g) and the mixture heated for 4 hours at 60° C. The reaction was quenched with water, extracted with ethyl acetate, washed with water (x2) and brine, dried (MgSO$_4$) and evaporated in vacuo. The residue was purified on silica gel eluting with 10% ethyl acetate/petroleum ether (60–80° C.) to give the title compound. $^1$H NMR (250 MHz,CDCl$_3$) δ 2.09 (1H, vbr s), 2.59–2.75 (2H, m), 3.35 (3H, s), 3.42–3.50 (2H, m), 3.54–3.64 (2H, m), 3.97 (1H, m), 4.62 (2H, s), 7.25–7.41 (5H, m), 7.76 (2H, s), 7.79 (1H, s).

b) (2S)-1-((3,5-Bis(trifluoromethyl)phenyl)methyloxy)-2-(N-(2'-methoxyethyl)-N-(4-chloro-2-butyne))amino-2-phenylethane The product from step (a) (0.6 g) was dissolved in dimethylformamide (6 ml) and added dropwise to a pre-heated (60° C.) solution of 1,4-dichloro-2-butyne (0.35 g) and potassium carbonate (0.59 g) in dimethylformamide (6 ml). The mixture was stirred for 4 hours and was then extracted with ethyl acetate and water. The organic layer was washed (H$_2$O, brine), dried (MgSO$_4$) and evaporated in vacuo. The residue was purified on a gravity silica column using 10% ethyl acetate/petroleum ether (60–80° C.) as eluant to give the title compound. $^1$H NMR (250 MHz, CDCl$_3$) δ 2.73 (2H, m), 3.23 (3H, s), 3.38 (2H, t, J=5.8 Hz), 3.48 (1H, s), 3.56 (1H, s), 3.70–3.76 (1H, m), 3.81–3.91 (2H, m), 4.09 (2H, m), 7.19–7.29 (5H, m), 7.58 (2H, s), 7.68 (1H, s).

c) (2S)-1-((3,5-Bis(trifluoromethyl)phenyl)methyloxy)-2-(2'-methoxyethyl)-N-(4-azido-2-butyne)amino-2-phenylethane The product from step (b) (100 mg) and sodium azide (16 mg) were stirred together in dimethylsulfoxide under nitrogen for 16 hours. The reaction mixture was partitioned between ammonium chloride and ethyl acetate (4:1). The organic layer was washed (H$_2$O, brine), dried (MgSO$_4$) and evaporated in vacuo. The residue was purified on a gravity silica column using 20% ethyl acetate/petroleum ether (60–80° C.) as eluant to give the title compound. $^1$H NMR (250 MHz,CDCl$_3$) δ 2.72–2.81 (2H, m), 3.30 (3H, s), 3.41–3.48 (2H, m), 3.60 (1H, m), 3.62 (1H, br s), 3.75–4.00 (5H, m), 4.56 (2H, s), 7.26–7.40 (5H, m), 7.64 (2H, s), 7.75 (1H, s).

d) 4-(N-((2-((3,5-Bis(trifluoromethyl)phenyl)methyloxy)-1-(S)-phenyl)ethyl-N-(2'-methoxyethyl))aminomethyl)-5-(N',N'-dimethylaminomethyl)-1,2,3-triazole The product from step (c) (100 mg) and dimethylamine (0.5 ml) in 1,4-dioxane (2 ml) was heated with stirring in a sealed tube at 70° C. for 5 hours. The reaction mixture was then cooled and evaporated in vacuo. The residue was purified on a gravity silica column using 10%–20% methanol/ethyl acetate as eluant to give the title compound. $^1$H NMR (250 MHz,CDCl$_3$) δ 2.13 (6H, s), 2.66–2.75 (1H, m), 2.82–2.92 (1H, m), 3.27 (3H, s), 3.37–3.44 (4H, m), 3.77–3.83 (2H, m), 3.88–3.96 (2H, m), 4.05 (1H, t, J=6.29 Hz), 4.54 (2H, s), 7.19–7.27 (5H, m), 7.64 (2H, s), 7.72 (1H, s). MS (ES)=559.

I claim:

1. A compound of the formula (I):

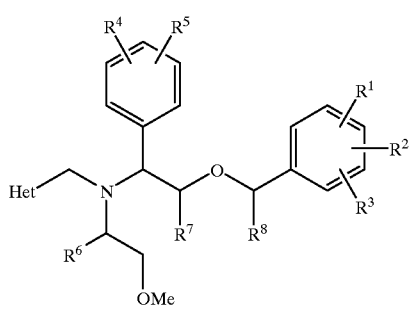

(I)

wherein

R$^1$ represents hydrogen, halogen, C$_{1-6}$alkyl, C$_{2-6}$alkenyl, C$_{2-6}$alkynyl, C$_{3-7}$cycloalkyl, C$_{3-7}$cycloalkylC$_{1-4}$alkyl, C$_{1-6}$alkoxy, C$_{1-4}$alkyl substituted by a hydroxy or C$_{1-4}$alkoxy group, OCF$_3$, hydroxy, trifluoromethyl, trimethylsilyl, nitro, CN, SR$^a$, SOR$^a$, SO$_2$R$^a$, COR$^a$, CO$_2$R$^a$ or CONR$^a$R$^b$ where R$^a$ and R$^b$ are each independently hydrogen or C$_{1-4}$alkyl;

R$^2$ and R$^3$ each independently represent hydrogen, halogen, C$_{1-6}$alkyl, C$_{1-4}$alkoxy, C$_{1-6}$alkoxy substituted by a C$_{1-4}$alkoxy group, or trifluoromethyl;

R$^4$ represents hydrogen, halogen, C$_{1-6}$alkyl, C$_{2-6}$alkenyl, C$_{2-6}$alkynyl, C$_{3-7}$cycloalkyl, C$_{3-7}$cycloalkylC$_{1-4}$alkyl, C$_{1-6}$alkoxy, C$_{1-4}$alkyl substituted by a hydroxy or C$_{1-4}$alkoxy group, OCF$_3$, hydroxy, trifluoromethyl, trimethylsilyl, nitro, CN, SR$^a$, SOR$^a$, SO$_2$R$^a$, COR$^a$, CO$_2$R$^a$, CONR$^a$R$^b$ where R$^a$ and R$^b$ are as previously defined;

R$^5$ represents hydrogen, halogen, C$_{1-6}$alkyl, C$_{1-6}$alkoxy substituted by a C$_{1-4}$alkoxy group, or trifluoromethyl;

R$^6$, R$^7$ and R$^8$ each independently represent hydrogen or a C$_{1-4}$alkyl group optionally substituted by a hydroxy group;

Het represents triazole optionally substituted by =O, =S or a C$_{1-4}$alkyl group, and optionally substituted by a group of the formula ZNR$^9$R$^{10}$ where Z is C$_{1-6}$alkylene or C$_{3-6}$cycloalkyl;

R$^9$ is hydrogen or C$_{1-4}$alkyl, C$_{3-7}$cycloalkyl, C$_{3-7}$cycloalkylC$_{1-4}$alkyl, or C$_{2-4}$alkyl substituted by C$_{1-4}$alkoxy or hydroxyl;

R$^{10}$ is hydrogen or C$_{1-4}$alkyl, C$_{3-7}$cycloalkyl, C$_{3-7}$cycloalkylC$_{1-4}$alkyl, or C$_{2-4}$alkyl substituted by C$_{1-4}$alkoxy, hydroxyl or a 4, 5 or 6 membered heteroaliphatic ring containing one or two heteroatoms selected from N, O and S;

or R$^9$, R$^{10}$ and the nitrogen atom to which they are attached form a heteroaliphatic ring of 4 to 7 ring atoms, optionally substituted by one or two groups selected from hydroxy or C$_{1-4}$alkoxy optionally substituted by a C$_{1-4}$alkoxy or hydroxyl group, and optionally containing a double bond, which ring may optionally contain an oxygen or sulphur ring atom, a group S(O) or S(O)$_2$ or a second nitrogen atom which will be part of a NH or NR$^c$ moiety where R$^c$ is C$_{1-4}$alkyl optionally substituted by hydroxy or C$_{1-4}$alkoxy;

or R$^9$, R$^{10}$ and the nitrogen atom to which they are attached form a non-aromatic azabicyclic ring system of 6 to 12 ring atoms;

or Z, R$^9$ and the nitrogen atom to which they are attached form a heteroaliphatic ring to 4 to 7 ring atoms which may optionally contain an oxygen ring atom;

or a pharmaceutically acceptable salt thereof.

2. A compound as claimed in claim 1 wherein R$^1$ is hydrogen, C$_{1-4}$alkyl, C$_{1-4}$alkoxy, halogen or CF$_3$.

3. A compound as claimed in claim 1 wherein R$^2$ is hydrogen, C$_{1-4}$alkyl, C$_{1-4}$alkoxy, halogen or CF$_3$.

4. A compound as claimed in claim 1 wherein R$^3$ is hydrogen, fluorine, chlorine or CF$_3$.

5. A compound as claimed in claim 1 wherein R$^1$ and R$^2$ are in the 3 and 5 positions of the phenyl ring.

6. A compound as claimed in claim 1 wherein R$^4$ is hydrogen and R$^5$ is hydrogen or 4-fluoro.

7. A compound as claimed in claim 1 wherein R$^6$ and R$^7$ are each independently hydrogen or methyl.

8. A compound as claimed in claim 1 wherein R$^8$ is hydrogen or C$_{1-2}$alkyl optionally substituted by a hydroxy group.

9. A compound as claimed in claim 1 wherein Het represents triazole which is unsubstituted or substituted with =O or —ZNR$^9$R$^{10}$.

10. A compound as claimed in claim 9 wherein Het is:

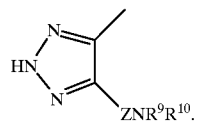

11. A compound as claimed in claim 1 wherein Z is CH$_2$ or CH$_2$CH$_2$ and NR$^9$R$^{10}$ is amino, methylamino, dimethylamino, diethylamino, azetidinyl, pyrrolidino or morpholino.

12. A compound of the formula (Ia):

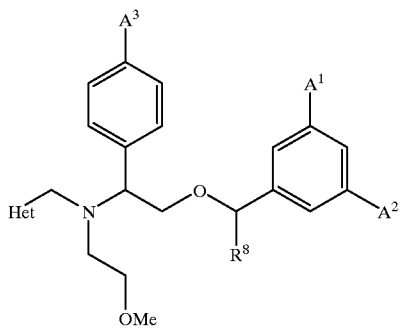

wherein:

$R^8$ represents hydrogen or a $C_{1-4}$alkyl group optionally substituted by a hydroxy group;

Het represents triazole optionally substituted by =O, =S or a $C_{1-4}$alkyl group, and optionally substituted by a group of the formula $ZNR^9R^{10}$ where Z is $C_{1-6}$alkylene or $C_{3-6}$cycloalkyl and $NR^9R^{10}$ is amino, methylamino, dimethylamino, diethylamino, azetidinyl, pyrrolidino or morpholino;

$A^1$ is fluorine or $CF_3$;

$A^2$ is fluorine or $CF_3$; and $A^3$ is hydrogen or fluorine;

or a pharmaceutically acceptable salt thereof.

13. The compound:

4-(N-((2-((3,5-bis(trifluoromethyl)phenyl)methyloxy)-1-(S)-phenyl)ethyl-N-(2'-methoxyethyl))aminomethyl)-5-(N',N'-dimethylaminomethyl)-1,2,3-triazole; or a pharmaceutically acceptable salt thereof.

14. A pharmaceutical composition comprising a compound as claimed in claim 1 in association with a pharmaceutically acceptable carrier or excipient.

15. A method for the treatment or prevention of pain or inflammation which method comprises administration to a patient in need thereof of an effective amount of a compound according to claim 1 or a pharmaceutically acceptable salt thereof.

16. A method for the treatment or prevention of migraine which method comprises administration to a patient in need thereof of an effective amount of a compound according to claim 1 or a pharmaceutically acceptable salt thereof.

17. A method for the treatment or prevention of emesis which method comprises administration to a patient in need thereof of an effective amount of a compound according to claim 1 or a pharmaceutically acceptable salt thereof.

18. A method for the treatment or prevention of postherpetic neuralgia which method comprises administration to a patient in need thereof of an effective amount of a compound according to claim 1 or a pharmaceutically acceptable salt thereof.

19. A process for the preparation of a compound as claimed in claim 1, which comprises (A) reacting a compound of formula (II)

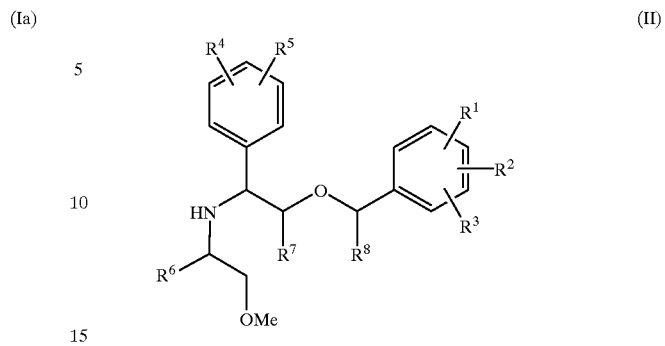

wherein $R^1$, $R^2$, $R^3$, $R^4$, $R^5$, $R^6$, $R^7$ and $R^8$ are as defined in claim 1 with a compound of formula (III):

where Het' is a group of the formula Het as defined in claim 1 or a precursor therefor and LG is a leaving group selected from an alkyl- or arylsulphonyloxy group or a halogen atom; and, if Het' is a precursor group, converting it to a group Het; or (B), where Het represents 1,2,3-triazol-4-yl substituted by $CH_2NR^9R^{10}$, by reaction of a compound of formula (V)

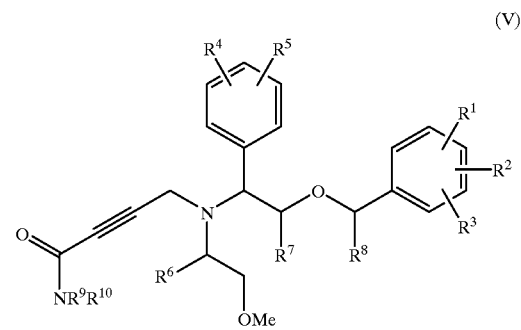

with an azide, followed by reduction of the carbonyl group adjacent to —$NR^9R^{10}$ using a suitable reducing agent; or (C), where Het represents 1,2,3-triazol-4-yl substituted by $CH_2NR^9R^{10}$, by reaction of a compound of formula (VI)

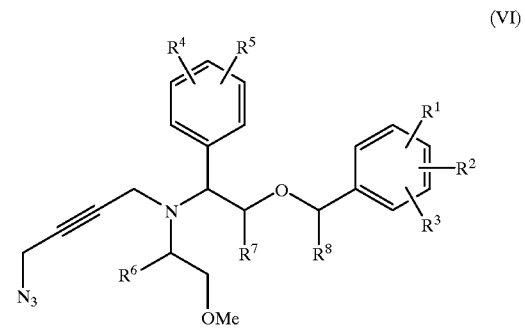

with an amine of formula $NHR^9R^{10}$; or (D), where Het represents substituted or unsubstituted 1,3,5-triazine by reaction of intermediates of formula (VII):

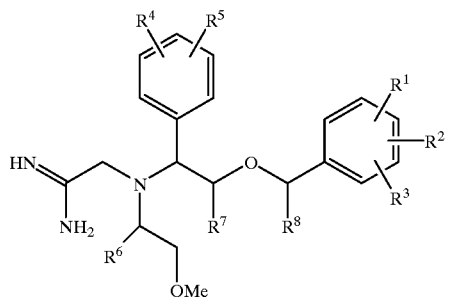

with substituted or unsubstituted 1,3,5-triazine; or
(E), where Het represents substituted or unsubstituted 1,2,4-triazine by reaction of an intermediate of formula (VIII) with a dicarbonyl compound of formula (IX):

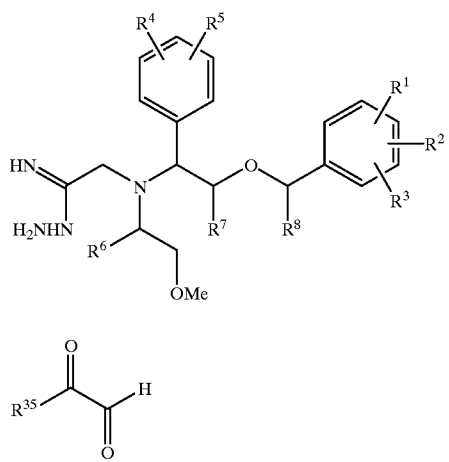

wherein $R^{35}$ represents H or $ZNR^9R^{10}$; or
(F), where Het represents a substituted 1,2,4-triazolyl group by reaction of an intermediate of formula (II) with a compound of formula (X)

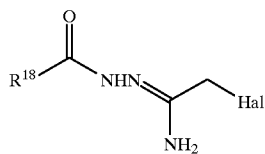

wherein Hal is a halogen atom, and $R^{18}$ is H, $CONH_2$ or $OCH_3$ (which is converted to an oxo substituent under the reaction conditions), in the presence of a base, followed where necessary by conversion to a compound of formula (I); or
(G), where Het represents thioxotriazolyl from intermediates of formula (XI)

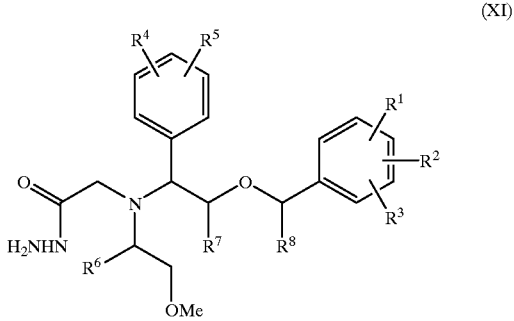

by reaction with a compound of formula HNCS, in the presence of a base;
each process being followed, where necessary, by the removal of any protecting group where present;
and when the compound of formula (I) is obtained as a mixture of enantiomers or diastereoisomers, optionally resolving the mixture to obtain the desired enantiomer;
and/or, if desired, converting the resulting compound of formula (I) or a salt thereof, into a pharmaceutically acceptable salt thereof.

* * * * *